United States Patent [19]
Desmurs et al.

[11] Patent Number: 4,822,922
[45] Date of Patent: Apr. 18, 1989

[54] STABILIZATION OF MIXTURES OF CHLORINATION OF PHENOL/CHLOROPHENOLS

[75] Inventors: Jean-Roger Desmurs, Saint-Symphorien d'Ozon; Serge Ratton, Villefontaine, both of France

[73] Assignee: Rhone-Poulenc Chimie, Courbevoie, France

[21] Appl. No.: 100,844

[22] Filed: Sep. 25, 1987

[30] Foreign Application Priority Data

Sep. 25, 1986 [FR] France ............................... 86 13557

[51] Int. Cl.$^4$ .............................................. C07C 37/38
[52] U.S. Cl. ...................... 568/702; 568/755; 568/774
[58] Field of Search ...................... 568/702, 774, 755; 252/182, 400.24

[56]  References Cited
U.S. PATENT DOCUMENTS

| 2,716,139 | 8/1955 | Dietzler | 568/702 |
| 2,752,398 | 6/1956 | Riley | 568/702 |
| 3,760,010 | 9/1973 | Widiger, Jr. | 568/755 |
| 3,839,463 | 10/1974 | Cohn | 568/755 |
| 4,160,112 | 7/1979 | Levek et al. | 568/755 |
| 4,289,587 | 9/1981 | Christena | 568/702 |
| 4,523,041 | 7/1985 | Kawa et al. | 568/755 |

FOREIGN PATENT DOCUMENTS

| 0123233 | 10/1984 | European Pat. Off. | |
| 262063 | 3/1988 | European Pat. Off. | 568/702 |
| 262061 | 3/1988 | European Pat. Off. | 568/702 |
| 958804 | 3/1950 | France. | |

*Primary Examiner*—Werren B. Lone
*Attorney, Agent, or Firm*—Burns, Doane, Swecker & Mathis

[57]  ABSTRACT

Mixtures produced by chlorination of phenol/chlorophenols are effectively stabilized by stirring same in the presence of a stabilizing amount of at least one strong protonic acid and/or a Lewis acid.

15 Claims, No Drawings

STABILIZATION OF MIXTURES OF CHLORINATION OF PHENOL/CHLOROPHENOLS

CROSS-REFERENCE TO RELATED APPLICATIONS

Our copending applications, Ser. No. 100,783 and Ser. No. 101,013, filed concurrently herewith and both assigned to the assignee hereof.

BACKGROUND OF THE INVENTION

1. Field of the Invention

The present invention relates to the stabilization of reaction mixtures produced during the chlorination of phenol and/or chlorophenols into tri-, tetra- and pentachlorophenols.

2. Description of the Prior Art

During the chlorination of phenol, monochlorophenols and dichlorophenols to produce trichlorophenols, tetrachlorophenols or pentachlorophenol, chlorination mixtures are obtained which are colored and which change upon passage of time. Thus, even during cold storage, an increase in the level of chlorophenoxyphenols and a change in the concentration of certain of the chlorophenols are observed, in particular.

When such chlorination mixtures are distilled, the distillation products also reflect this instability.

In these chlorination mixtures, the present applicants have now determined that the presence of unsaturated cyclic ketones containing a gem-dichloro substituent appears to be the source of the change, or instability, in these mixtures.

SUMMARY OF THE INVENTION

Accordingly, a major object of the present invention is the provision of improved means for avoiding the problem of instability of chlorination mixtures of the aforesaid type.

Briefly, the present invention features the stabilization of reaction mixtures produced via the chlorination of phenol and/or chlorophenols, by stirring such mixtures in the presence of an effective stabilizing amount of at least one strong protonic acid and/or a Lewis acid.

DETAILED DESCRIPTION OF THE PREFERRED EMBODIMENTS OF THE INVENTION

More particularly according to the present invention, by "strong protonic acid" there is intended a protonic acid having an acidity function Ho of less than or equal to $-5$.

Exemplary of such strong protonic acids, representative are sulfuric acid, perchloric acid, trifluoromethanesulfonic acid, chlorosulfonic acid, fluorosulfonic acid, pyrosulfuric acid and also acidic resins containing fluorosulfonic functional groups.

The term "strong protonic acids" also includes the acid forms of the aluminosilicates, the acid forms of the clays, and of the silicas.

Among the acid aluminosilicates, the zeolites and molecular sieves are particularly representative, and among the acid clays, the bentonites are similarly particularly representative.

By "Lewis acid", there is intended its usual definition, i.e., compounds which accept electron pairs.

Those Lewis acids noted in the text edited by G. A. OLAH "Friedel-Crafts and related Reactions", Volume I, pages 191 to 197 (1963), are particularly representative.

Lewis acids suitable for use in the process of this invention are more especially the halides of the elements of Groups 3a, 4a, 5a, 1b, 2b, 3b, 4b, 5b, 6b, 7b and 8 of the Periodic Table which are liquid or solid under the subject operating conditions, such as chlorides, bromides, fluorides and iodides of aluminum, gallium, tin, phosphorus, antimony, arsenic, bismuth, titanium, tantalum, tellurium, selenium, zirconium, hafnium, vanadium, samarium, niobium, tungsten, platinum, molybdenum, iron, cobalt, nickel, zinc and cadmium.

As specific examples of such halides, representative are aluminum chloride, aluminum bromide, ferric chloride, ferric bromide, titanium tetrachloride, zirconium tetrachloride, platinum chloride, vanadium trichloride, samarium chloride, tellurium chloride, selenium chloride, antimony pentafluoride, bismuth trichloride, stannic chloride, gallium trichloride, hafnium tetrachloride and phosphorus tribromide.

Certain of the Lewis acids, the chlorides of the elements mentioned above, can be prepared in situ by introducing the said element into the chlorination mixture.

The gem-dichlorinated unsaturated cyclic ketones are principally gem-dichlorinated cyclohexadienones incidentally containing 1, 2, 3 or 4 other chlorine atoms on different carbon atoms of the benzene ring, and gem-dichlorinated cyclohexenones also incidentally containing 1 to 6 other chlorine atoms on different carbon atoms of the benzene ring.

These are, on the one hand, 4,4-dichloro-2,5-cyclohexadienones and 6,6-dichloro-2,4-cyclohexadienones containing, in addition, 1 to 4 chlorine atoms.

Exemplary of the principal such gem-dichlorinated cyclohexadienones, representative are:
6,6-dichloro-2,4-cyclohexadienone,
4,4-dichloro-2,5-cyclohexadienone,
2,4,4,6-tetrachloro-2,5-cyclohexadienone,
2,4,6,6-tetrachloro-2,4-cyclohexadienone,
2,3,4,4,6-pentachloro-2,5-cyclohexadienone,
2,4,5,6,6-pentachloro-2,4-cyclohexadienone,
2,3,4,6,6-pentachloro-2,4-cyclohexadienone,
2,3,4,4,5,6-hexachloro-2,5-cyclohexadienone, and
2,3,4,5,6,6-hexachloro-2,4-cyclohexadienone.

These are, on the other hand, 2,2-dichloro-3-cyclohexenones, 6,6-dichloro-2-cyclohexenones, 4,4-dichloro-2-cyclohexenones and 6,6-dichloro-3-cyclohexenones containing, in addition, 1 to 6 chlorine atoms.

Exemplary of the principal such gem-dichlorinated cyclohexenones, representative are:
2,4,5,6,6-pentachloro-2-cyclohexenone,
2,4,4,5,6,6-hexachloro-2-cyclohexenone,
2,2,4,5,6,6-hexachloro-3-cyclohexenone,
2,4,4,5,5,6,6-heptachloro-2-cyclohexenone,
2,2,3,4,5,6,6-heptachloro-3-cyclohexenone,
2,3,4,4,5,5,6-heptachloro-2-cyclohexenone,
2,3,4,4,5,6,6-heptachloro-2-cyclohexenone,
2,3,4,4,5,5,6,6-octachloro-2-cyclohexenone, and
2,2,3,4,5,5,6,6-octachloro-3-cyclohexenone.

The temperature at which the mixture that is produced by the chlorination of phenol and/or chlorophenols and the strong acid or acids and/or Lewis acid or acids is stirred varies over wide limits, for example, from 20° C. to 200° C.

Preferably, however, in order to effect good reaction, the temperature will range from 40° C. to 180° C. and more preferably from 60° C. to 150° C.

The duration of the treatment is highly variable depending upon the temperature, the amount of gem-dichlorinated cyclic ketones present in the mixture and the strong acid or Lewis acid employed. It may vary, for example, from a few minutes to several tens of hours.

In general, it ranges from 1 hour to 15 hours, although these figures are not of critical importance.

The amount of strong acid and/or Lewis acid depends, quite obviously, on the content of gem-dichlorinated cyclic ketones in the mixture and on the nature of which. These ketones are generally assayed in the mixture by liquid chromatography using double detection: an ultraviolet detector for all of the compounds in the mixture collectively, and an electrochemical detector specifically for the gem-dichlorinated cyclic ketones; or by an overall assay using electrochemistry.

(i) 2,4,6-trichlorophenol: 1.97 g (0.010 mole);
(ii) 2,4,4,6-tetrachloro-2,5-cyclohexadienone: 0.23 g (0.001 mole);
(iii) acid compound: amount shown in Table I.

The mixture was heated under stirring for 8 hours (except for Example 16, in which the duration was 24 hours) at 70° C. (except for Example 15, in which the temperature was 125° C.).

The reaction mass was analyzed by liquid chromatography, using double detection with UV (totality of the chlorinated compounds) and amperometry (gem-dichlorinated unsaturated cyclic ketones).

Under the same conditions, a control test was performed with the same charges, except for the acid compound.

Table I below reflects the nature and the amount of acid compound used, as well as the results of the analyses performed after the treatment.

% DC=degree of conversion.
% YLD=yield with respect to the chlorocyclohexadienone converted.

TABLE I

| TEST | Acid compound: amount used | % DC of the chlorocyclo-hexadienone | YLD of 2,4,6-trichloro-phenol | % YLD of 2,3,4,6-tetrachlorophenol | YLD of pentachloro-phenol | Chlorophenoxy-phenols (in mmol) |
|---|---|---|---|---|---|---|
| Control A | None | 2 | 0 | 0 | 0 | 0 |
| Example 1 | CF$_3$SO$_3$H: 2.5 mmol | 100 | 0 | 78.4 | 0 | 0 |
| Example 2 | CF$_3$SO$_3$H: 0.48 mmol | 100 | 0 | 78.4 | 0 | 0 |
| Example 3 | CF$_3$SO$_3$H: 0.13 mmol | 100 | 0 | 72.3 | 0 | 0 |
| Example 4 | AlCl$_3$: 2.5 mmol | 100 | 0 | 78.7 | 0 | 0.325 |
| Example 5 | AlCl$_3$: 0.031 mmol | 100 | 0 | 64.9 | 0 | 0 |
| Example 6 | AlCl$_3$: 0.31 mmol | 100 | 0 | 71.3 | 0 | 0 |
| Example 7 | ZrCl$_4$: 2.5 mmol | 100 | 0 | 100 | 0 | 0 |
| Example 8 | SiO$_2$: 2.5 mmol | 33 | 0 | 23 | 0 | 0 |
| Example 9 | bentonite: 0.25 g dried 6 hr at 200° C. | 66 | 0 | 17 | 0 | 0 |
| Example 10 | Te: 0.50 mmol | 100 | 0 | 94 | 0 | 0.37 |
| Example 11 | ZrCl$_4$: 2.5 mmol | 100 | 0 | 100 | 0 | 0.37 |
| Example 12 | Se: 2.5 mmol | 100 | 0 | 36 | 0 | 0.37 |
| Example 13 | PtCl$_4$: 2.5 mmol | 100 | 0 | 89 | 0 | 0.24 |
| Example 14 | VCl$_3$: 2.5 mmol | 74.3 | 0 | 16 | 0 | 0 |
| Example 15 | SmCl$_3$.6H$_2$O: 2.5 mmol | 93 | 0 | 36.4 | 0 | 0 |
| Example 16 | SiO$_2$: 2.5 mmol | 73 | 0 | 57 | 0 | 0.06 |

To attain good stabilization of the chlorination mixtures, it is necessary to introduce an amount of strong acid and/or Lewis acid at least equal to 0.05 mole per 1 mole of gem-dichlorinated cyclic ketones.

Since it is not always easy to determine accurately the nature of the different gem-dichlorinated unsaturated cyclic ketones in the chlorination mixtures, it is preferable to introduce an amount of strong acid and/or Lewis acid comprising from 0.2 to 10 moles per mole of gem-dichlorinated unsaturated cyclic ketones.

In order to further illustrate the present invention and the advantages thereof, the following specific examples are given, it being understood that same are intended only as illustrative and in nowise limitative.

EXAMPLES 1 TO 16

A 10-cm$^3$ glass reactor equipped with a stirrer was charged with the following materials:

EXAMPLES 17 TO 22

The reactor described in Examples 1 to 16 was charged with the following materials:
(i) 2,3,4,4,6-pentachloro-2,5-cyclohexadienone: 0.265 g (0.001 mole);
(ii) 2,4,6-trichlorophenol (or 2,3,4,6-tetrachlorophenol): 0.010 mole;
(iii) acid compound: 0.0025 mole.

The procedure was described in Examples 1 to 16.
Duration of the tests: 8 hours at 70° C.

Table II below reflects the nature of the phenolic compound and of the acid compound used, as well as the results of the analyses performed after the treatment.

TABLE II

| TEST | Chlorophenol acid compound | % DC of the chlorocyclo-hexadienone | % YLD of 2,3,4,6-tetrachlorophenol | YLD of pentachloro-phenol | Chlorophenoxy-phenols (in mmol) |
|---|---|---|---|---|---|
| Control B | 2,4,6-trichloro-phenol none | 27 | 11.2 | 0 | 0 |
| Control C | 2,3,4,6-tetra- | 7 | 0 | 0 | 0 |

TABLE II-continued

| TEST | Chlorophenol acid compound | % DC of the chlorocyclo-hexadienone | % YLD of 2,3,4,6-tetrachlorophenol | YLD of pentachloro-phenol | Chlorophenoxy-phenols (in mmol) |
|---|---|---|---|---|---|
| | chlorophenol none | | | | |
| Example 17 | 2,4,6-trichloro-phenol AlCl$_3$ | 100 | 88.0 | 0 | 0.17 |
| Example 18 | 2,4,6-trichloro-phenol FeCl$_3$ | 100 | 50 | 0 | 0.17 |
| Example 19 | 2,4,6-trichloro-phenol TiCl$_4$ | 95.9 | 29 | 58.9 | 0 |
| Example 20 | 2,4,6-trichloro-phenol CF$_3$SO$_3$H | 100 | 10 | 67.9 | 0 |
| Example 21 | 2,4,6-trichloro-phenol H$_2$SO$_4$ | 70.7 | 42.9 | 29 | 0 |
| Example 22 | 2,3,4,6-tetra-chlorophenol AlCl$_3$ | 100 | 0 | 74.3 | 0 |

EXAMPLES 23 TO 26

A 10-cm$^3$ glass reactor equipped with a stirrer was charged with the following materials:
(i) 2,4,6-trichlorophenol or 2,3,4,6-tetrachlorophenol: 0.010 mole;
(ii) 2,3,4,4,5,6-hexachloro-2,5-cyclohexadienone: 0.30 g (0.001 mole);
(iii) acid compound: 0.0025 mole.

The procedure was as in Examples 1 to 16, for 8 hours at 70° C.

Table III below reflects the nature of the phenolic compound and of the acid compound used, as well as the results of the analyses performed after the treatment.

EXAMPLES 27 TO 38

A 30-cm$^3$ glass reactor placed in an oven at 70° C. and incorporating a magnetic stirrer was charged with the following materials:
(i) 2,4,4,6-tetrachloro-2,5-cyclohexadiene-1-one: 0.70 g;
(ii) 2,4,6-trichlorophenol: 5.93 g;
(iii) acid compound: 0.10 g.

The reaction mass was melted before the reactor was placed in the oven. The course of the reaction was followed by withdrawing samples.

Table IV below reflects the nature of the acid compound used, as well as the results of the analyses performed after the treatment.

TABLE III

| TEST | Chlorophenol acid compound | % DC of the chlorocyclo-hexadienone | % YLD of pentachlorophenol | Chlorophenoxy-phenols (in mmol) |
|---|---|---|---|---|
| CONTROL D | 2,4,6-trichlorophenol none | 2 | 2 | 0 |
| Example 23 | 2,4,6-trichlorophenol AlCl$_3$ | 100 | 100 | 0 |
| Example 24 | 2,4,6-trichlorophenol CF$_3$SO$_3$H | 100 | 99 | 0 |
| Control E | 2,3,4,6-tetrachlorophenol none | 2 | 2 | 0 |
| Example 25 | 2,3,4,6-tetrachlorophenol AlCl$_3$ | 100 | 100 | 0 |
| Example 26 | 2,3,4,6-tetrachlorophenol CF$_3$SO$_3$H | 100 | 100 | 0 |

TABLE IV

| TEST | Acid compound | Duration | % DC of the chlorocyclo-hexadienone | % YLD of 2,4,6-trichlorophenol | % YLD of tetrachloro-phenol | % chloro-phenols by weight |
|---|---|---|---|---|---|---|
| Control A | None | 8 hr | 2 | 0 | 0 | 0 |
| Example 27 | ZrCl$_4$ | 30 min | 100 | 0 | 78.3 | 2.2 |
| Example 28 | TiCl$_4$ | 60 min | 30.4 | 0 | 35.0 | 1.4 |
| Example 29 | HfCl$_4$ | 15 min | 100 | 0 | 80.3 | 0 |
| Example 30 | ClSO$_3$H | 30 min | 100 | 0 | 70.0 | 0 |
| Example 31 | FeCl$_3$ | 30 min | 100 | 0 | 71.8 | 3.0 |
| Example 32 | FeBr$_3$ | 30 min | 100 | 0 | 59.4 | 1.2 |
| Example 33 | GaCl$_3$ | 15 min | 100 | 0 | 80.1 | 3.0 |
| Example 34 | AlCl$_3$ | 15 min | 100 | 0 | 68.7 | 10.0 |
| Example 35 | AlBr$_3$ | 15 min | 100 | 0 | 15.8 | 13.0 |
| Example 36 | PBr$_3$ | 30 min | 46.6 | 0 | 35.4 | 0 |
| Example 37 | TeCl$_4$ | 60 min | 100 | 0 | 72.5 | 1.0 |

TABLE IV-continued

| TEST | Acid compound | Duration | % DC of the chlorocyclo-hexadienone | % YLD of 2,4,6-trichlorophenol | % YLD of tetrachloro-phenol | % chloro-phenols by weight |
|---|---|---|---|---|---|---|
| Example 38 | SbCl$_3$ | 15 min | 100 | 0 | 84.1 | 5.0 |

While the invention has been described in terms of various preferred embodiments, the skilled artisan will appreciate that various modifications, substitutions, omissions, and changes may be made without departing from the spirit thereof. According, it is intended that the scope of the present invention be limited solely by the scope of the following claims, including equivalents thereof.

What is claimed is:

1. A process for the stabilization of a reaction mixture produced by the chlorination of at least one of a phenol and a chlorophenol, which mixture contains at least one gem-dichlorinated cyclic ketone, comprising stirring said mixture in the presence of an effective stabilizing amount of at least one of a strong protonic acid and a Lewis acid.

2. The process as defined by claim 1, comprising stirring such mixture in the presence of a protonic acid having an acidity function Ho of less than or equal to −5.

3. The process as defined by claim 2, said strong protonic acid comprising sulfuric acid, perchloric acid, trifluoromethanesulfonic acid, chlorosulfonic acid, fluorosulfonic acid, pyrosulfuric acid, or an acidic resin containing fluorosulfonic groups.

4. The process as defined by claim 1, comprising stirring such mixture in the presence of an acid form of an aluminosilicate, an acid form of a clay, or an acid form of a silica.

5. The process as defined by claim 4, comprising stirring such mixture in the presence of a zeolite, molecular sieve, bentonite or silica.

6. The process as defined by claim 1, comprising stirring such mixture in the presence of a halide of an element of Groups 3a, 4a, 5a, 1b, 2b, 3b, 4b, 5b, 6b, 7b and 8 of the Periodic Table.

7. The process as defined by claim 6, comprising stirring such mixture in the presence of a chloride, bromide, fluoride or iodide of aluminum, gallium, tin, phosphorus, antimony, arsenic, bismuth, titanium, tantalum, tellurium, selenium, zirconium, hafnium, vanadium, samarium, niobium, tungsten, platinum, molybdenum, iron, cobalt, nickel, zinc or cadmium.

8. The process as defined by claim 7, comprising stirring such mixture in the presence of aluminum chloride, aluminum bromide, ferric chloride, ferric bromide, titanium tetrachloride, zirconium tetrachloride, platinum chloride, vanadium trichloride, samarium chloride, tellurium chloride, selenium chloride, antimony pentafluoride, bismuth trichloride, stannic chloride, gallium trichloride, hafnium tetrachloride or phosphorus tribromide.

9. The process as defined by claim 6, wherein said halide is prepared in situ by introducing the corresponding metal into the mixture of chlorination.

10. The process as defined by claim 1, said stirring being carried out at a temperature of from 20° C. to 200° C.

11. The process as defined by claim 1, said stirring being carried out at a temperature of from 40° C. to 180° C.

12. The process as defined by claim 1, said stirring being carried out at a temperature of from 60° C. to 150° C.

13. The process as defined by claim 1, wherein the mole ratio of acid to gem-dichlorinated cyclic ketones is at least 0.05.

14. The process as defined by claim 13, said mole ratio ranging from 0.2 to 5.

15. The product of the process as defined by claim 1.

* * * * *